United States Patent [19]

Chou et al.

[11] Patent Number: 4,665,168

[45] Date of Patent: May 12, 1987

[54] CEPHALOSPORIN INTERMEDIATE

[75] Inventors: Ta-Sen Chou; Perry C. Heath, both of Indianapolis, Ind.

[73] Assignee: Eli Lilly and Company, Indianapolis, Ind.

[21] Appl. No.: 852,003

[22] Filed: Apr. 14, 1986

[51] Int. Cl.$^4$ .................................... C07D 501/18
[52] U.S. Cl. .......................................... 540/224
[58] Field of Search ................ 544/24, 25; 540/224

[56] References Cited

U.S. PATENT DOCUMENTS

| | | | |
|---|---|---|---|
| 3,207,755 | 9/1965 | Abraham et al. | 260/243 |
| 3,270,012 | 8/1966 | Higgens | 260/243 |
| 3,280,118 | 10/1966 | Eardley et al. | 260/243 |
| 3,498,979 | 3/1970 | Crisp et al. | 260/243 |
| 3,520,884 | 7/1970 | Sharp et al. | 260/243 |
| 3,577,412 | 5/1971 | Spencer et al. | 260/243 |
| 3,790,565 | 2/1974 | Vanevenhoven | 260/243 C |
| 4,369,313 | 1/1983 | Jones et al. | 544/24 |

*Primary Examiner*—Nicholas S. Rizzo
*Attorney, Agent, or Firm*—William B. Scanlon; Leroy Whitaker

[57] ABSTRACT

7-Amino-3-pyridiniummethyl (and substituted pyridiniummethyl)-3-cephem-4-carboxylic acid hydrothiocyanate salts and a process for the preparation thereof are provided. The salts are useful for recovering the pyridinium nuclei from reaction mixtures in which they are formed or used.

8 Claims, No Drawings

CEPHALOSPORIN INTERMEDIATE

BACKGROUND OF THE INVENTION

This invention relates to intermediates for the preparation of cephalosporin antibiotics. In particular, it relates to 7-amino-3-pyridiniummethyl-3-cephem-4-carboxylic acid hydrothiocyanate salt and 7-amino-3-(substituted-pyridiniummethyl)-3-cephem-4-carboxylic acid hydrothiocyanate salts and to a process for preparing the hydrothiocyanate salts.

The semi-synthetic cephalosporin antibiotics are often prepared by the N-acylation of the appropriate 7-amino-3-cephem nucleus compound. Among the semi-synthetic cephalosporins that can be prepared in this manner are the 7-acylamino-3-quaternary ammoniummethyl-3-cephem-4-carboxylate antibiotics, e.g., cephaloridine and ceftazidime. The 3'-pyridinium nuclei useful in the synthesis are, therefore, valuable intermediates for such antibiotics. The availability of these nuclei in stable, non-hygroscopic form is highly desirable and could allow for bulk storage of the nucleus intermediate for later use in preparing the desired antibiotic.

SUMMARY

7-Amino-3-pyridiniummethyl-3-cephem-4-carboxylic acid hydrothiocyanate salt and 7-amino-3-(substituted-pyridiniummethyl)-3-cephem-4-carboxylic acid hydrothiocyanate salts are provided. The salts are stable, non-hydrated salts possessing low water solubility which are useful for purifying, storing and isolating the 3'-pyridinium nuclei.

The hydrothiocyanate salts of the invention are readily formed in aqueous solutions of the nuclei, or in aqueous solutions of water-soluble nuclei salts, from which they precipitate in crystalline form.

The hydrothiocyanate salts of the invention are useful intermediates for preparing antibiotics such as cephaloridine, ceftazidime and related compounds.

DETAILED DESCRIPTION

The nucleus hydrothiocyanate salts provided herein are represented by the formula 1

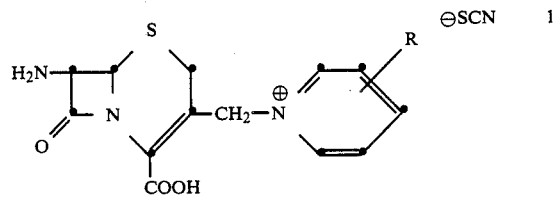

wherein R is hydrogen, $C_1$–$C_4$ alkyl, halogen, trifluoromethyl, $C_1$–$C_4$ alkoxy, hydroxy, hydroxymethyl, $C_1$–$C_4$ alkylthio, cyano or carbamoyl.

Examples of 7-amino nucleus hydrothiocyanate salts represented by the formula 1 are 7-amino-3-pyridiniummethyl-3-cephem-4-carboxylic acid, 7-amino-3-(4-ethylpyridinium)methyl-3-cephem-4-carboxylic acid, 7-amino-3-(3-chloropyridinium)methyl-3-cephem-4-carboxylic acid, 7-amino-3-(4-methoxypyridinium)methyl-3-cephem-4-carboxylic acid, 7-amino-3-(3-trifluoromethylpyridinium)methyl-3-cephem-4-carboxylic acid, 7-amino-3-(4-methylthiopyridinium)methyl-3-cephem-4-carboxylic acid, 7-amino-3-(3-methylthiopyridinium)methyl-3-cephem-4-carboxylic acid, 7-amino-3-(4-cyanopyridinium)methyl-3-cephem-4-carboxylic acid, 7-amino-3-(4-carbamoylpyridinium)methyl-3-cephem-4-carboxylic acid, 7-amino-3-(3-carbamoylpyridinium)methyl-3-cephem-4-carboxylic acid and 7-amino-3-(4-hydroxymethylpyridinium)methyl-3-cephem-4-carboxylic acid hydrothiocyanate salts.

The hydrothiocyanate salts are best obtained by the process of this invention. According to the process, the compounds of the invention are prepared by adding an alkali metal thiocyanate to an aqueous solution of the 7-amino nucleus compound at a pH between 1.5 and 2.5, preferably pH 2. The hydrothiocyanate salts generally precipitate from the aqueous medium at about room temperature. Cooling the solution below room temperatures can aid crystallization and enhance yields of the salt.

The concentration of the 7-amino nucleus compound in the aqueous medium is generally between about 5% to about 35% by weight. An amount of alkali metal thiocyanate salt in excess of two equivalents is added and preferably an excess of two to three equivalents are used. The alkali metal thiocyanate can be dissolved in water and the solution mixed with the solution of the 7-amino nucleus compound.

Suitable alkali metal thiocyanates are sodium thiocyanate, potassium thiocyanate and lithium thiocyanate with potassium thiocyanate being preferred. Other sources of HSCN may also be used to prepare the salts of the invention.

The preparation of the hydrothiocyanate salts is best carried out by first adjusting the pH of the 7-amino nucleus solution to a pH of about 4.0 to 4.5 with potassium phosphate, sodium phosphate, or other suitable buffer, adding an aqueous solution of potassium thiocyanate and, after addition, acidifying the solution to about pH 2 with a mineral acid, e.g., hydrochloric acid. For example, 1.72 g of 7-amino-3-pyridiniummethyl-3-cephem-4-carboxylate dihydrochloride dihydrate is dissolved in 18 ml of water and a solution of 7.34 g of potassium thiocyanate in water is added with stirring. The pH of the solution is adjusted to about pH 2 with hydrochloric acid and the precipitated 7-amino-3-pyridiniummethyl-3-cephem-4-carboxylic acid hydrothiocyanate is filtered and dried. The crystallization mixture may be stirred in the cold prior to filtration to enhance the yield of salt.

The hydrothiocyanate salts represented by the formula 1 are useful forms of the quaternary ammonium nuclei and can be used to isolate these nuclei from crude mixtures in which they are prepared. For example, the nuclei can be formed by the N-deacylation of a 7-acylamino-3-pyridiniummethyl-3-cephem-4-carboxylate compound, e.g., cephaloridine or a substituted cephaloridine, represented by the following formula

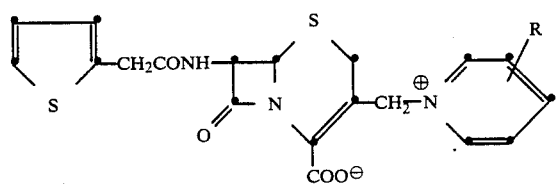

wherein R has the same meanings as defined above for formula 1. Treatment of the 7-acylamino-3-pyridiniummethyl compound in a chlorinated hydrocarbon solvent with a phosphorus halide such as $PCl_5$ provides the imino chloride of the amido side chain. The imino chloride is converted to the corresponding imino ether on treatment with an alcohol such as methyl alcohol, and the imino ether is hydrolyzed to the 7-amino nucleus compound. Additional water is added to the deacylation mixture and the aqueous phase containing the nucleus is separated and is treated with an alkali metal thiocyanate as described above to precipitate the hydrothiocyanate salt represented by the formula 1.

Alternatively, the 7-amino-3-quaternary ammonium nuclei can be obtained as shown below with 7-ACA via N-formylation to 7-formamidocephalosporanic acid, displacement of the 3'-acetoxy group thereof with pyridine or a substituted pyridine followed by deformylation.

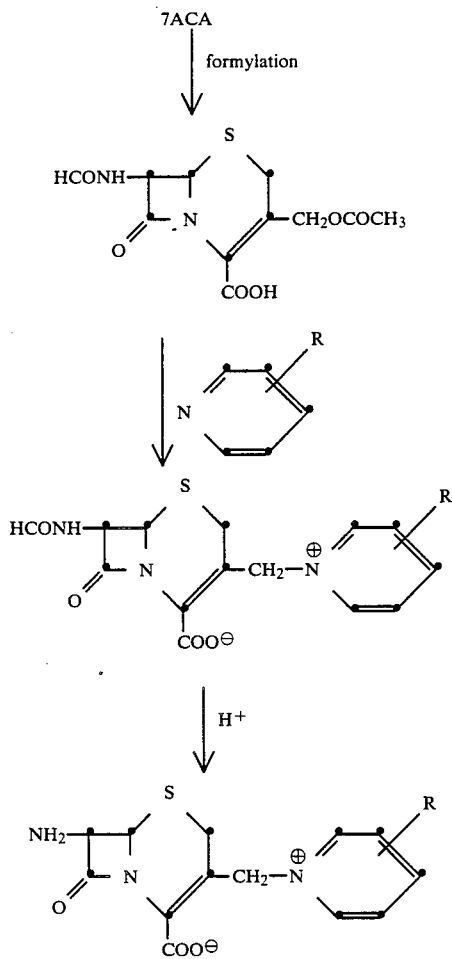

The N-deformylation step above is best carried out in methanolic-HCl. Following hydrolysis, the hydrolysis mixture is diluted with water and the nucleus hydrothiocyanate salt isolated as described hereinabove.

The process of this invention also can be used to recover the unreacted pyridinium nuclei from reaction mixtures such as mixtures resulting from N-acylations of the nuclei where incomplete acylation has occurred.

Accordingly, the hydrothiocyanate salts of the invention are useful for recovering such nuclei from crude reaction mixtures in which they are prepared or used.

The salts of the invention can be N-acylated to provide the desired 7-acylamino-3-quaternary pyridinium-3-cephem-4-carboxylate antibiotic. For example, a solution of 2-(2-tritylaminothiazol-4-yl)-2-[2-(t-butyloxycarbonyl)propoxyimino]acetyl chloride in methylene chloride containing triethyl amine is added to a solution of 7-amino-3-pyridiniummethyl-3-cephem-4-carboxylic acid thiocyanate salt in dimethylacetamide or dimethylformamide containing triethylamine to provide 7β-[[2-(2-tritylaminothiazol-4-yl)-2-[2-(t-butyloxycarbonyl)-propoxyimino]acetamido]]-3-pyridiniummethyl-3-cephem-4-carboxylate. Removal of the trityl and t-butyl protecting groups by known procedures provides the antibiotic known as ceftazidime.

A preferred hydrothiocyanate salt of this invention is 7-amino-3-pyridiniummethyl-3-cephem-4-carboxylic acid (formula 1, R=H). Other preferred salts are represented by the formula 1 when R is chloro, cyano, methylthio or carbamoyl.

This invention is further described by the following examples.

EXAMPLE 1

7-Amino-3-pyridiniummethyl-3-cephem-4-carboxylic acid dihydrochloride dihydrate (20 g) was dissolved in 80 ml of water and the pH of the solution was adjusted to 4 with 45% potassium phosphate. Potassium thiocyanate (9.72 g) was added to the solution and the pH adjusted to 2 with 2N hydrochloric acid. The acidified solution was cooled with stirring in an ice bath for one hour. The crystallized hydrothiocyanate salt was filtered, washed with water and with acetone and was dried overnight under vacuum at 40° C. There were obtained 15.56 g of crystalline 7-amino-3-pyridiniummethyl-3-cephem-4-carboxylic acid hydrothiocyanate salt having the following characteristics.

Percent Elemental Composition Calculated for $C_{14}H_{14}N_4O_3S_2$: Theory: C, 47.99; H, 4.03, N, 15.99; O, 13.70; S, 18.30. Found: C, 47.94; H, 4.07; N, 15.74; O, 13.92; S, 18.30.

IR (KBr): 2078 cm$^{-1}$ (HSCN) and 1792 cm$^{-1}$ (β-lactam)

| UV (95% C$_2$H$_5$OH): | λ max | ε max |
|---|---|---|
| | 203 nm | 4200 |
| | 258 nm | 3600 |

EXAMPLE 2

The following hydrothiocyanate salts are prepared by the method described in Example 1 by substituting the corresponding substituted-3-pyridinium nucleus for the unsubstituted pyridinium nucleus of Example 1.

(a) 7-amino-3-(3-chloropyridiniummethyl)-3-cephem-4-carboxylic acid.

(b) 7-amino-3-(3-carbamoylpyridiniummethyl)-3-cephem-4-carboxylic acid.

(c) 7-amino-3-(4-carbamoylpyridiniummethyl)-3-cephem-4-carboxylic acid.

(d) 7-amino-3-(4-cyanopyridiniummethyl)-3-cephem-4-carboxylic acid.

We claim:

1. A compound of the formula in solid form

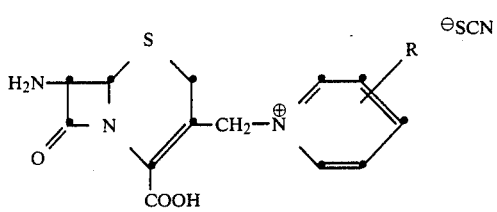

wherein R is hydrogen, $C_1$–$C_4$ alkyl, halogen, trifluoromethyl, hydroxy, $C_1$–$C_4$ alkoxy, hydroxymethyl, $C_1$–$C_4$ alkylthio, cyano or carbamoyl.

2. The compound of claim 1 wherein R is hydrogen, chloro, cyano, methylthio or carbamoyl.

3. The compound of claim 2 wherein R is hydrogen.

4. A process for preparing the hydrothiocyanate salt of claim 1 which comprises the steps of (1) adjusting the pH of an aqueous solution of a 7-amino compound of the formula

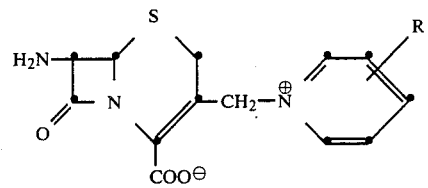

wherein R is hydrogen, halogen, $C_1$–$C_4$ alkyl, trifluoromethyl, hydroxy, $C_1$–$C_4$ alkoxy, hydroxymethyl, $C_1$–$C_4$ alkylthio, cyano or carbamoyl to between about 4.0 and about 4.5;

(2) mixing said solution with an alkali metal thiocyanate in an amount of at least 2 moles per mole of said 7-amino compound; and (3) acidifying said mixture to a pH between about 1.5 and about 2.5.

5. The process of claim 4 comprising the further step of separating said hydrothiocyanate salt.

6. The process of claim 4 where in step 1 the pH is adjusted with potassium phosphate.

7. The process of claim 4 where in said 7-amino compound R is hydrogen, chloro, cyano, methylthio or carbamoyl.

8. The process of claim 7 wherein R is hydrogen.

* * * * *